United States Patent [19]

Széles

[11] Patent Number: 4,601,905

[45] Date of Patent: Jul. 22, 1986

[54] SKIN REGENERATING COMPOSITION AND A PROCESS FOR THE PREPARATION THEREOF

[75] Inventor: Lajos Széles, Dombóvár, Hungary

[73] Assignee: Interag RT, Budapest, Hungary

[21] Appl. No.: 356,221

[22] Filed: Mar. 8, 1982

[30] Foreign Application Priority Data

Mar. 17, 1981 [HU] Hungary .................................. 662/81

[51] Int. Cl.$^4$ ............................................. A61K 35/78
[52] U.S. Cl. ..................................... 424/195.1
[58] Field of Search ........................................ 424/195

[56] References Cited

PUBLICATIONS

Steinmetz, Codex Vegetabilis, No. 978, and 917 1957.

*Primary Examiner*—Jerome D. Goldberg
*Assistant Examiner*—John W. Rollins, Jr.
*Attorney, Agent, or Firm*—Karl F. Ross; Herbert Dubno

[57] ABSTRACT

A process for the preparation of a skin-regenerating or skin-protecting pharmaceutical composition is disclosed wherein the flower, root, fruit or cortex of a plant selected from the group consisting of Fugaceae, Caesalpiniaceae, Chenopodiaceae, and Rosaceae is extracted with ethanol at a temperature of 0° to 50° C. The obtained plant extract is purified and the dry substance content thereof is adjusted to 0.01 to 0.1% by adding more of the ethanol.

14 Claims, No Drawings

SKIN REGENERATING COMPOSITION AND A PROCESS FOR THE PREPARATION THEREOF

The subject of our invention is a skin regenerating, skin treating and protecting composition which can successfully be used as household medicine or cosmetics.

No reliable household remedy has been suggested for excoriation, until now, which is perfectly harmless and the components of which are of natural origin and can safely be stored in households and even laymen can use it. Such excoriation can be considered as a result of sun-bathing, kitchen or laboratory work, bites by insects or rubbing of allergic skin-itching, bruise, shock, simple burns. In such cases in order to promote epithelization the surface should be covered and to avoid infection disinfection and temporary relief of pain, contraction of blood vessels and then epithelization are required.

The subject of our invention is an epithelizing, skin treating, regenerating, protecting composition prepared by extracting one or more plants or parts of plants belonging to Caesalpiniaceae and/or Fagaceae and/or Chenopodinaceae and/or Rosaceae plant family under aerobic or anaerobic circumstances—optionally in several stages—until the dry substance content stops increasing. Then the obtained extract—which is optionally filtered and/or submitted to fractionated distillation and/or chromatography—is adjusted to 0.01 to 0.10% by weight of dry substance concentration by adding ethanol.

According to our invention different parts of plants can be used as plant drug depending on the quality of the plant and its type. So the following parts of plants can be used, ripe fruit or parts thereof, stone or parts thereof, skin, pulp or skin of fruit, furthermore flower of plant or certain parts of the flower, such as stamen, petal, peduncle of flower, furthermore bark of certain plants or its certain parts such as e.g. the inner parts. Root or tuber can also be used.

According to our invention the above plants or parts of plants can also be used in mixtures. One can also proceed by extracting only one part separately until the required dry substance content is achieved. The obtained extracts will be mixed and diluted together upto the requested concentration. We can also proceed by mixing the parts and extracting the mixture.

The plant parts are preferably chopped to pieces. Extraction can be carried out at atmosphere pressure or at over-pressure. The temperature of the extraction is preferably between 0° 50° C.

Extraction can be carried out by any known extraction method. Choice depends on the scale of the process. Continuous or semi-continuous or discontinuous methods, turbo-extraction, digestion, percolation can be used. Extraction may be followed by taking small samples at every stage, which are carefully evaporated in vacuum and finally the dry substance content is determined. Should it not grow any longer, extraction can be finished.

When extraction is terminated, the solution is filtered. Extraction is carried out with 70–100% ethanol and preferably carried out with 96 to 100% alcohol and sterile filtration is used, because in this case our composition can be applied for more serious epithelial injuries just as well.

Some plant drugs are outlined hereinafter which, according to our invention, can be used alone or optionally can be submitted to extraction as a mixture, respectively, its extracts can be mixed: *Crataegi oxyacanthae* fructus, *Rosae gallicae* perianthium, *Pruni spinosae* fructus, *Rubi idaei* fructus, *Betae vulgaris* radix (cv, conditiva), *Quercus roburis* cortex, *Quercus petraeae* cortex, *Ratanchiae radix, Rosae chinensis* perianthium, *R. multiflorae* perianthium, *Rosae damascenae* perianthium, *R. pendulinae* perianthium, *Crataegi monogynae* fructus, *Malus pumilae* fructus (exocarpium).

Naturally, the above enumeration includes several subcases, as several subgroups can be ranged under the above plant groups. Should such kind of plant be applied which contains undesired material from the point of view of use (e.g. it cannot be applied to the surface of the skin, or has an unpleasant smell), the undesired material may be removed by distillation or chromatography.

If desired the obtained extract can be purified by distillation. One may proceed also by purifying only one or the other extract made from different plants by distillation and alcoholic resolution by which the undesired components may be removed.

For a similar purpose extracts can also be submitted to chromatography before mixing and diluting same with ethanol to the desired concentration.

The solution prepared according to our invention is to be finished so that it can directly be applied on the surface of the skin, optionally after addition of certain additives. Coloring agents, scenting materials or well known disinfectants, possibly antibiotics can be applied as additives.

The solution should be suitable for painting or for bathing but it can also be prepared as a spray. The use of a spray is preferred because it protects skin surface without touching the skin surface directly.

The composition according to our invention can preferably be used for assuaging of pain on the skin caused by sun-bathing for too long and for promoting epithelization. The plant extract forms a protective layer on the damaged surface or on the surface to be protected; furthermore it protects the damaged surface from the air, and from impurities but at the same time it has a smoothing effect on the skin, it relieves itching, a burning feeling, and promotes airing and epithelization. It shows a moderate bactericidal activity. In case of blistered injuries caused by burns or chemicals it promotes removal of discharge and crust formation. If it is used in due time blistering, long lasting skin change, and keloid-formation can be avoided.

The composition according to our invention is to be used as follows: dangerous, strange materials causing injuries should be removed from the surface of the skin or neutralized. Materials with a causing effect or a hot material (e.g. spattered fat or oil, hot dishes or drinks, possibly household acids or alkalis, chemicals, hot iron, etc.) should be washed or wiped. The composition of the invention should be sprinkled, painted or possibly poured on the skin surface. Within 4–5 hours the application can be repeated.

The composition according to the invention can be used as a household remedy at working places, in households, in "kindergarten", in schools but it can also be used to protect or to restore the healthy skin of animals with special respect to animals whose skin and fur is of great value. No expert is required when it is used for treating simple injuries, excoriation. It assures epithelization on the damaged surface, and furthermore the growth of hair. It is advisable to use it after sun-bathing.

Further details of our invention will be illustrated by the following Examples which serve merely for illustration and not for limitation.

The plant parts and procedures are arranged in separate groups in the Examples. They are interchangeable and variable.

EXAMPLE 1

A composition is prepared having the following components:
Caesalpiniaceae family:
  Ratanchiae radix—max. 1% b.w.
Rosaceae family: Prunoidae subfamily:
  *Pruni spinosae* fructus—max. 20% b.w.
Rosoideae subfamily:
  *R. gallicae* perianthium—min. 79% b.w.

Picked plant parts are separated manually from optionally present strange materials and ill plant-parts. Care should be taken in selecting pure plant-parts. If necessary plant-parts are washed.

Procedure

On 20 kg. of selected plant parts 60 l of 96% 1$^{st}$ class ethanol are poured and it is maintained at room temperature. The mother lye is moved so that it becomes deareated and the drug wet. Care should be taken that the extracting agent covers the whole amount of the plant parts. A tank is to be kept covered at room temperature for 14 days. It is to be moved daily and alcohol can be supplied if required. During this procedure fire-regulations should be observed. After 14 days the supernatant is decanted and the plant parts slightly pressed. These two extracts are filtered through filter-paper after homogenization and stored in cool place. Max. storage time of the concentrate is 5 years.

The final product is to be prepared from the stock solution as follows: the stock solution is diluted with 96% 1$^{st}$ class ethanol, its dry substance content should be min. 0.03%, then it is homogenized and sterile filtered through membrane-filter. It is filled in bottles or finished as spray.

EXAMPLE 2

A drug is prepared having the following components:
Rosaceae family: Pomoideae subfamily:
  *Crataegi oxycanthae* fructus—max. 0.5% b.w.
Fagaceae family:
  *Quercus petraeae sessiflorae* cortex—max. 0.5% b.w.
Rosoideae subfamily:
  *R. gallicae* perianthium—40% b.w.
Prunoideae subfamily:
  *Rubi idaei* fructus—7% b.w.
Chenopodinaceae family:
  *Betae vulgaris* (cv. conditiva) radix—52% b.w.
Plant parts were selected as described in Example 1.

Procedure

On 10 kg. selected drug 120 l of 96% ethanol are poured, then it is extracted at 60 r.p.m. under stirring at room temperature for 4 hours.

Then it is decanted, the drug is slightly pressed, the obtained extracts are filtered through filter-paper after homogenization and stored in dark, cool place. One may further proceed as described in Example 1.

EXAMPLE 3

A drug is prepared having the following components:
Rosaceae family: Maloideae subfamily:
  *Crataegi monogynae* fructus—max. 0.4% b.w.
  *Crataegi oxyacanthae* fructus—max. 0.6% b.w.
Rosoideae subfamily:
  *R. gallicae* perianthium—min. 85% b.w.
  *R. multiflorae* perianthium cv.—max. 14% b.w.

Procedure 10 l. of 70% ethanol are added to 1 kg. of selected plant parts. It is stirred in a rotating extractor at 30 r.p.m. for 4 hours. Then it is decanted, the drug is slightly pressed, the two extracts are filtered through filter-paper after homogenization, purified by chromatography, and stored in a dark cool place.

One may further proceed as described in Example 1.

EXAMPLE 4

A composition is prepared having the following components:
Fagaceae family:
  *Querci robur* or *Querci petraea* cortex—max. 0.3% b.w.
Rosaceae family:
Caesalpiniaceae family:
  Ratanchiae radix—max. 0.3% b.w.
Prunoideae subfamily:
  *Rubi idaei* fructus—max. 11% b.w.
  *Pruni spinosae* fructus—max. 8% b.w.
Rosoideae subfamily:
  *R. gallicae* cv. perianthium—max. 75% b.w.
  *R. chinensis* cv. perianthium—max. 5% b.w.

To 1 kg. of the selected plant parts 10 l. of 100% ethanol are added. Then it is extracted on a vibroextractor at 10000 r.p.m. for 1 min. After sedimentation it is decanted, the sediment is slightly pressed, the two extracts are filtered after homogenization through filter paper and then evaporated in vacuum to half volume. The residue is stored at a cool place. One may further proceed according to Example 1.

EXAMPLE 5

A drug is prepared having the following components:
Fagaceae family:
  *Quercus robur* cortex—max. 0.3% b.w.
Caesalpiniaceae family:
  Ratanchiae radix—max. 0.3% b.w.
Rosoideae subfamily:
  *Rosae pendulinae* perianthium—max. 0.5% b.w.
  *Rosae damascenae* perianthium—max. 0.8% b.w.
  *Rosae gallicae* perianthium—max. 87% b.w.

1 kg. of the selected drug is filled to a percolator of suitable size. Percolator is fed with 96% ethanol. Then the percolator is operated for 72 hours in and outflow is adjusted to 100 ml./hour. After the extraction percolator is emptied, the drug is slightly pressed. The two extracts are filtered through filter-paper and stored in dark, cool place.

One may further proceed as disclosed in Example 1.

EXAMPLE 6

Using the same process as in Example 5 the following composition is used:
Rosaceae family: Maloideae subfamily:
  *Malus pumilae* fructus (exocarpium)—max. 0.4% b.w.

*Crataegi oycanthae* fructus—max. 0.5% b.w.
Rosoidae subfamily:
- *R. gallicae* perianthium—min. 85% b.w.
- *R. multiflorae* perianthium cv.—max. 14% b.w.

I claim:

1. A process for the preparation of a sterile alcoholic extract used as a skin-regenerating or skin-protecting pharmaceutical composition, which comprises the steps of:
   (a) extracting the flower, root, fruit or cortex of at least one plant belonging to the Rosaceae family at a temperature of 0° to 50° C. with ethanol of 70 to 100% purity to obtain a plant extract;
   (b) subjecting the plant extract to sterile filtration; and
   (c) adjusting the plant extract to 0.01 to 0.1% by weight of dry substance content by adding more of the ethanol.

2. The process defined in claim 1 wherein step (a) is carried out using ethanol of a purity of 96 to 100%.

3. The process defined in claim 1 wherein prior to step (a), the plant flower, root, fruit or cortex is chopped to pieces.

4. The process defined in claim 1, step (a), in that several plants or parts of plants are separately extracted, and the extracts are mixed.

5. The process defined in claim 1, step (a), in that several plants or parts of plants are extracted together.

6. The process defined in claim 1, step (a), wherein the plant belonging to the Rosaceae family is selected from the group consisting of the Rosoideae subfamily, Prunoideae subfamily, and Maloideae subfamily.

7. The process defined in claim 6, wherein the Rosoideae subfamily member is selected from the group which consists of *Rosae gallicae* perianthium, *Rosae multiflorae* perianthium, *Rosae chinensis* perianthium, *Rosae pendulinae* perianthium and *Rosae damascenae* perianthium.

8. The process defined in claim 6 wherein the Prunoideae subfamily is selected from the group consisting of *Pruni spinosae* fructus and *Rubi idaei* fructus.

9. The process defined in claim 6 wherein the Maloideae subfamily is selected from the group which consists of *Malus pumilae* fructus and *Crataegi oxycanthae* fructus.

10. The process defined in claim 1 wherein the extracted plants include at least two different members of the Rosaceae family.

11. The process defined in claim 10 wherein the extracted plants from the Rosaceae family include at least one plant from the Maloideae subfamily and at least one plant from the Rosoideae subfamily.

12. The process defined in claim 1 wherein the plants extracted include the flower, root, fruit or cortex of at least one member of the Rosaceae family, and the flower, root, fruit or cortex of at least one of the Fagaceae family, the Chenopodinaceae family or the Caesalpiniaceae family.

13. The process defined in claim 1, wherein in step (a), the weight ratio of the extracting ethanol to the plant parts ranges between 3:1 and 12:1.

14. A skin-regenerating or skin-protecting pharmaceutical composition obtained by the process defined in claim 1.

* * * * *